(12) United States Patent
Yuan et al.

(10) Patent No.: US 10,463,513 B2
(45) Date of Patent: Nov. 5, 2019

(54) BIODEGRADABLE METALLIC VASCULAR STENT AND APPLICATION THEREOF

(71) Applicant: SHANGHAI JIAO TONG UNIVERSITY, Shanghai (CN)

(72) Inventors: Guangyin Yuan, Shanghai (CN); Chenxin Chen, Shanghai (CN); Wei Wu, Shanghai (CN); Migliavacca Francesco, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 39 days.

(21) Appl. No.: 15/554,206

(22) PCT Filed: Apr. 29, 2016

(86) PCT No.: PCT/CN2016/080642
§ 371 (c)(1),
(2) Date: Aug. 28, 2017

(87) PCT Pub. No.: WO2017/012386
PCT Pub. Date: Jan. 26, 2017

(65) Prior Publication Data
US 2018/0078395 A1    Mar. 22, 2018

(30) Foreign Application Priority Data

Jul. 20, 2015 (CN) .......................... 2015 1 0427276

(51) Int. Cl.
*A61F 2/915* (2013.01)
*A61F 2/06* (2013.01)
*A61F 2/88* (2006.01)

(52) U.S. Cl.
CPC ................ *A61F 2/915* (2013.01); *A61F 2/06* (2013.01); *A61F 2/88* (2013.01);
(Continued)

(58) Field of Classification Search
CPC .............. A61F 2/915; A61F 2210/0004; A61F 2002/91575
See application file for complete search history.

(56) References Cited

U.S. PATENT DOCUMENTS 5,800,526 A * 9/1998 Anderson ................. A61F 2/07
606/191
2009/0030506 A1 * 1/2009 Klocke ..................... A61F 2/86
623/1.46
(Continued)

FOREIGN PATENT DOCUMENTS

| CN | 2621712 Y | 6/2004 |
|---|---|---|
| CN | 2936196 Y | 8/2007 |

(Continued)

*Primary Examiner* — Yashita Sharma
*Assistant Examiner* — Rebecca S Preston

(57) ABSTRACT

A biodegradable metallic vascular stent includes: a base body which is tubular with a lumen along a longitudinal axis, wherein the base body has a plurality of circumferential support structures which are successively positioned along the longitudinal axis. The circumferential support structures are each composed of a sequence of repeat units and has two or more connectors, wherein two adjacent circumferential support structures are joined together by at least one of the connectors, and each of the connectors is attached to one of arched elements in the repeat units of the two adjacent circumferential support structures to be connected. The biodegradable metallic vascular stent possesses suited radial pressure, flexibility and fatigue strength. Furthermore, the stent is design for peripheral vascular disease and coronary artery disease treatment as well.

2 Claims, 2 Drawing Sheets

(52) U.S. Cl.
CPC ............ *A61F 2002/91533* (2013.01); *A61F 2002/91541* (2013.01); *A61F 2002/91575* (2013.01); *A61F 2002/91583* (2013.01); *A61F 2210/0004* (2013.01); *A61F 2250/0059* (2013.01); *A61F 2250/0067* (2013.01); *A61F 2310/00041* (2013.01)

(56) References Cited

U.S. PATENT DOCUMENTS

| | | | | |
|---|---|---|---|---|
| 2010/0131044 | A1* | 5/2010 | Patel | A61F 2/915 623/1.16 |
| 2012/0172972 | A1* | 7/2012 | Meyer | A61F 2/915 623/1.16 |
| 2013/0268045 | A1* | 10/2013 | Papp | A61F 2/958 623/1.11 |
| 2013/0304191 | A1* | 11/2013 | Cai | A61F 2/856 623/1.15 |

FOREIGN PATENT DOCUMENTS

| | | |
|---|---|---|
| CN | 102397590 A | 4/2012 |
| CN | 103110465 A | 5/2013 |

\* cited by examiner

BIODEGRADABLE METALLIC VASCULAR STENT AND APPLICATION THEREOF

CROSS REFERENCE OF RELATED APPLICATION

This is a U.S. National Stage under 35 U.S.C 371 of the International Application PCT/CN2016/080642, filed Apr. 29, 2016, which claims priority under 35 U.S.C. 119(a-d) to CN 201510427276.2, filed Jul. 20, 2015.

BACKGROUND OF THE PRESENT INVENTION

Field of Invention

The present invention is directed to a biodegradable stent with an improved stent design. The present invention further relates to a stent for peripheral vascular disease and coronary artery disease.

Description of Related Arts

The implantation of stents has become established as one of the most effective therapeutic measures in the treatment of vascular diseases. There are three stages of vascular stent development: bare metal stent, drug-eluting stent and biodegradable stent. Conventionally, the clinical application of vascular stents is mainly fabricated from stainless steel, nitinol and cobalt-chromium alloy, with drug-eluting polymer coating.

Drug-eluting stents can inhibit the regeneration of vascular smooth muscle cells due to the release of antiproliferative drugs, thereby reducing the rate of vascular restenosis. However, permanent metallic implants have specific drawbacks which limit their more widespread use. These limitations include long-term endothelial dysfunction, delayed re-endothelialization, thrombogenicity, permanent physical irritation, chronic inflammatory local reactions, and mismatches in mechanical behavior between stented and non-stented vessel areas, and importantly non-permissive or disadvantageous characteristics for later surgical revascularization. Since the major effect of stent implantation is provided by its scaffolding effect, it is required to last for 6-12 months during which arterial remodeling and healing is achieved. After this period, the presence of stent within the body cannot provide any beneficial effects. Presently, there are three different kinds of biodegradable stent: polymer vascular scaffold, iron-based stent and magnesium-based stent. Bioabsorbable polymer has been shown to possess acceptable biocompatibility, but a polymeric stent requires a greater strut thickness than most metal stents because of the polymer's lower ultimate tensile strength. Other limitations seen in polymer stents include the inability to expand completely with balloon dilatation along with restenosis rates similar to those observed for conventional bare metal stents. On another side, the corrosion of Fe-based alloys is generally too slow, as a result the implants would stay in human body for a too long time even after finishing their clinical role.

Magnesium stents are superior in comparison to their polymeric counterparts in terms of mechanical properties. Mg element present in the body are considered biocompatible and therefore uniform corrosion Mg alloys have been developed. With the complete degradation of Mg alloys after the vascular recovery, the long-term foreign-body reaction can be avoided. Furthermore, the suitable strength and toughness of Mg alloys make them admirable candidates as coronary stent.

The Chinese published patent CN103110465 discloses an Mg alloy stent with medium metal coverage, good radial strength and flexibility; another Chinese patent CN2936196Y discloses an Mg alloy stent with good mechanical property. Due to the inferior elongation capability of Mg alloy under room temperature, the crown contour with high curvature in the stent described in above two patents will be damaged during crimping and expanding deformation. The conventional uniform width struts cannot overcome the stress concentration factor, which will increase the stress corrosion rate in crucial part and decrease the corrosion fatigue life.

SUMMARY OF THE PRESENT INVENTION

An example embodiment of the present invention is a biodegradable metallic vascular stent, wherein the tubular base body with the structure element distinctive design provides a stent which allows minimize the maximum stress and plastic deformation in arched elements, with effective utilization of the space that is available for crimping. By means of improving the mechanical properties of biodegradable stent, including enough radial force and suitable corrosion rate, to meet the clinical requirements.

The present invention is achieved through the following technical solutions:

The present disclosure provides an example embodiment of a biodegradable metallic vascular stent, comprising a base body which is tubular with a lumen along the longitudinal axis, wherein the base body has a plurality of circumferential support structures which are successively positioned along the longitudinal axis and are each composed of a sequence of repeat units, and each of the circumferential support structures has two or more connectors, wherein two adjacent circumferential support structures are joined together by at least one of the connectors, and each of the connectors is attached to one of arched elements of the two adjacent circumferential support structures to be connected.

In a preferred embodiment, the adjacent circumferential support structures are specularly symmetric.

In a preferred embodiment, the connectors, which are "n" shaped, comprise curved elements and two straight elements; wherein outer contours are smooth curve-shaped, and inner contours are symmetric intersection of smooth curves.

In a preferred embodiment, in a circumferential direction of the circumferential support structures, a quantity of the repeat units is between 4 and 8.

In a preferred embodiment, the connectors are spiral distribution in a longitudinal direction; a quantity of the connectors between the two adjacent circumferential support structures to be connected is between 2 and 4.

In a preferred embodiment, the circumferential support structures are each composed of the sequence of the repeat units. And the repeat units are composed of arched elements, bump elements, diagonal elements and kink elements; the diagonal elements are symmetrical located at both side of the arched elements, wherein every two of the diagonal elements are joined together by one of the kink elements.

In a preferred embodiment, in the circumferential support structures, there is one of the bump elements at a center of an outer contour of each of the arched elements; a height of bump elements is between 0.01 mm and 1 mm; a major axis of the arched elements is between 0.1 mm and 0.5 mm, a minor axis of the arched elements is between 0.05 mm and 0.40 mm.

In a preferred embodiment, for the base body, an out diameter is between 1 mm and 5 mm, a thickness in a radial direction is between 0.1 mm and 0.3 mm, a length in a longitudinal direction is between 10 mm and 100 mm; wherein for the circumferential support structures, a width of the arched elements is between 0.1 mm and 0.3 mm, a width of diagonal elements is between 0.06 mm and 0.25 mm; wherein for the connectors, a radius of a middle line of curved elements is between 0.10 mm and 0.30 mm.

In a preferred embodiment, the base body is composed entirely of a biodegradable magnesium alloy or a biodegradable zinc alloy.

The present disclosure provides wherein the stent biodegradable metallic vascular can be applied to treatment of a peripheral vascular disease and a coronary artery disease.

Compared with the prior art, the present innovation has the following beneficial effects:

1. In the present invention, the biodegradable stent, with good biocompatibility and uniform-degradation, allows for successful acute revascularization of coronary artery stenosis. The main advantage of the biodegradable stent is that following complete biodegradable, no foreign body remains in the vessel wall at long term follow-up, which may avoid the increased long-term risk of stent thrombosis seen with the permanent stent.

2. Compared to permanent stents, such as stainless steel, cobalt-based alloys and titanium-based alloys, biodegradable magnesium alloy stents or zinc alloy stent has inferior mechanical performance and show corrosion damage during their life when implanted. The conventional design for permanent stents are not suitable for biodegradable stent under large crimping and expanding deformation. One example aim of the patent is to provide a stent design for biodegradable material to overcome the problems described above. Due to the characteristic repeat units design that kink elements, bump elements, non-uniform radius arched elements and gradient width diagonal elements are introduced and adequate organized, a homogeneous distribution of stress and plastic deformation in the arched elements of the stent are accomplished. Therefore, the biodegradable stent according to the embodiment possess sufficient radial force, good bending flexibility, uniform deformation and residual stress distribution.

3. The approach according to some embodiment of the present invention is optimal morph the shape and rim of arched elements, diagonal elements and kink elements. The out contours of diagonal elements are parallel to the longitudinal axis after crimping, by means of matching the bending stiffness between arched elements and kink elements, in order to make full use of the space, ensure the sufficient crimp ability and avoid the self-contact. Therefore, the plastic deformation distribution of circumferential support structures are unify and the recoil of stent after crimping is reduced.

4. As the result of the shape optimization for the repeat unit, it has been discovered that the stent according to this invention embodiment has the optimal transmission of force from the central area of inner edge of arched elements to the whole area of arched elements and adjacent diagonal elements. Owing to the homogeneous distribution of plastic deformation, the stress concentration and the corrosion rate of stent after deployed are reduced and Corrosion fatigue behaved of stent is improved.

5. The biodegradable stent according to the innovation can be applied to the treatment of peripheral vascular disease and coronary artery disease, but also can be used as other kinds of stents, such as esophageal stent, tracheal stent, biliary stent, pancreatic stent and catheters stents.

BRIEF DESCRIPTION OF THE DRAWINGS

By reading the following detailed description of non-limiting embodiments given with reference to the following drawings, the features, objects and advantages will become more apparent.

Element reference: 1—repeat unit; 2—connector; 3—circumferential support structure; 11—bump element; 12—arched element; 13—diagonal element; 14—kink element; 21—curved element; 22—straight portion.

DETAILED DESCRIPTION OF THE PREFERRED EMBODIMENT

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

Embodiment 1

Figure 1:
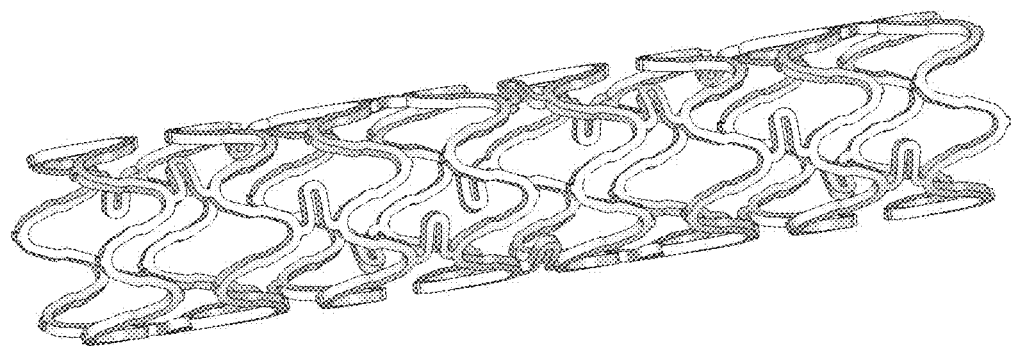
FIG. 1 shows a computer simulation illustration depicting a perspective view of an embodiment of a biodegradable stent.

The present disclosure provides an example embodiment 1 of a biodegradable stent shown in FIG. 1, comprising a base body which is tubular with a lumen along a longitudinal axis, wherein the base body has a plurality of circumferential support structures 3 which are successively positioned along the longitudinal axis and are each composed of a sequence of repeat units 1; and each of the circumferential support structures has two or more connectors 2, wherein two adjacent circumferential support structures 3 are joined together by at least two of the connector 2, and each of the connectors 2 is attached to one of arched elements 12 of the two adjacent circumferential support structures 3 to be connected.

According to embodiment 1, the adjacent circumferential support structures 3 are specularly symmetric.

Figure 4:
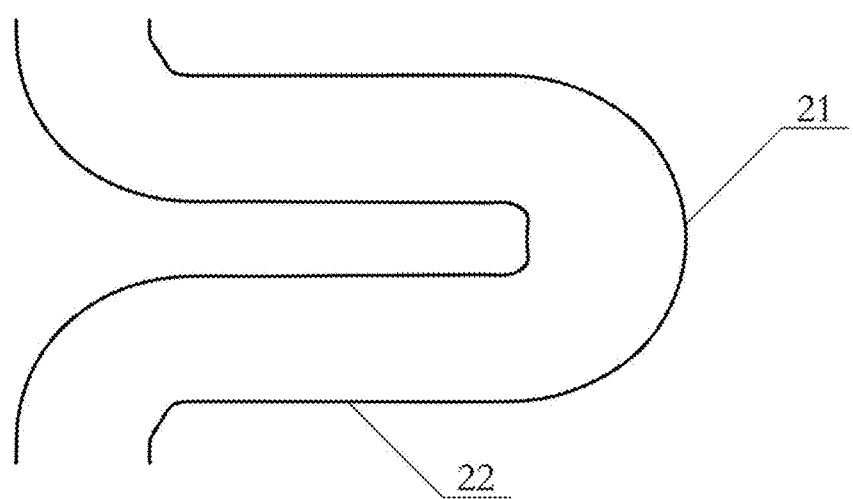
FIG. 4 shows the detailed shape of connector in an embodiment.

FIG. 4 shows the connectors 2, which are "n" shaped and comprise curved elements 21 and two straight elements 22; outer contours of curved element 21 are smooth curve-shaped, and inner contours are symmetric intersection of smooth curves.

As shown in FIG. 1, a quantity of the repeat units in each of the circumferential support structures 3 is between 4 and 8. In the embodiment 1, the quantity is 6; the connectors 2 are spiral distribution in a longitudinal direction; a quantity of the connectors 2 between the two adjacent circumferential support structures 3 to be connected is between 2 and 4. In the embodiment 1, the number is 3.

Figure 2:
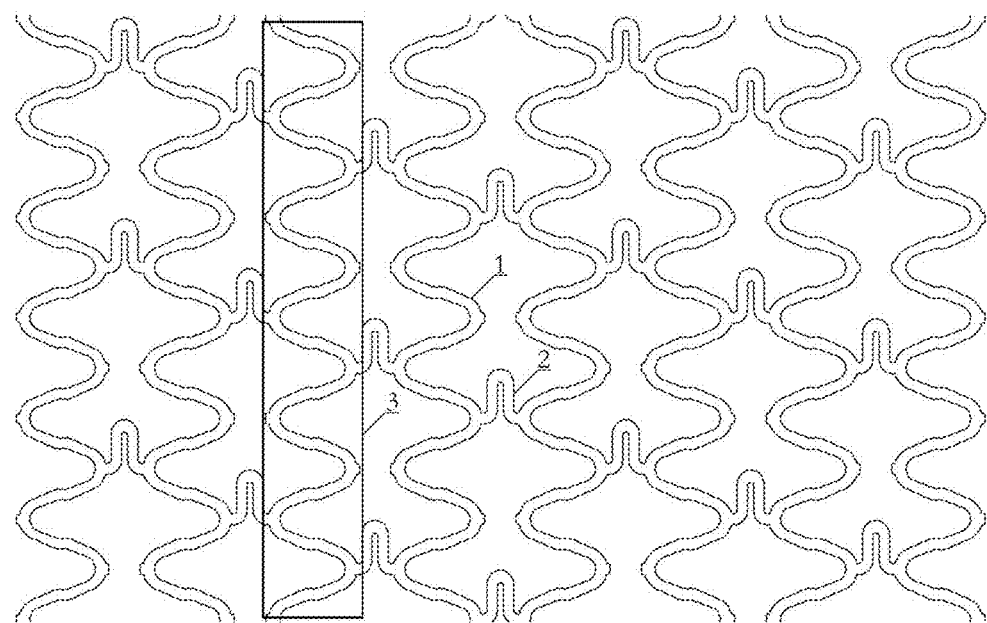
FIG. 2 shows a planar view of a stent scaffold embodiment.
Figure 3:
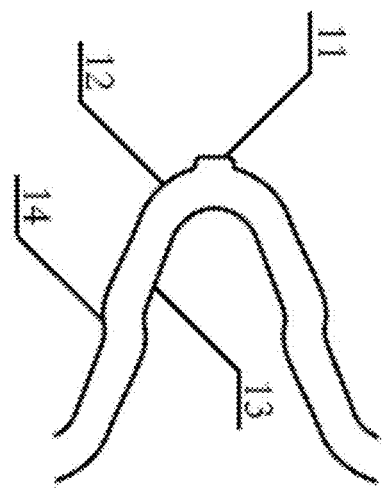
FIG. 3 shows the detailed shape of repeat unit in an embodiment.

FIG. 2 shows the detail shape of the repeat units 1, which is the repeat units 1 of the circumferential support structures 3. Specifically, the repeat units 1 are each composed of the sequence of the arched elements 12, diagonal elements 13 and kink elements 14; the diagonal elements 13 are symmetrical located at both side of the arched elements 12, wherein two of the diagonal elements 13 are joined together by one of the kink elements 14.

There is a bump element 11 at a center of the outer contour of each of the arched elements; a height of the bump elements 11 is between 0.01 mm and 1 mm; a major axis of the arched elements 12 is between 0.1 mm and 0.5 mm, a minor axis of the arched elements 12 is between 0.05 mm and 0.40 mm.

As shown in FIG. 1, an out diameter of the stent is between 1 mm and 5 mm, a thickness in a radial direction is between 0.1 mm and 0.3 mm, a length in a longitudinal direction is between 10 mm and 100 mm; wherein for the circumferential support structures 3, a width of the arched elements 12 is between 0.1 mm and 0.3 mm, a width of the diagonal elements 13 is between 0.06 mm and 0.25 mm; wherein for the connectors 2, a radius of a middle line of the curved elements 21 is between 0.10 mm and 0.30 mm.

Stent coating function to deliver anti-proliferative drugs, increase device biocompatibility and decrease the corrosion rate of Mg stent. The coating must also have suitable mechanical properties such that occurrences of delamination and fracture during stent crimping and implantation are eliminated. Owing to the homogeneous distribution of plastic deformation in the stent during crimping and balloon expansion, the stress and traction concentration of polymer coating reduced a lot and the integrity of coating is guaranteed. Furthermore, the corrosion fatigue performance of stent is improved.

The base body of the stent according to one invention embodiment may be composed of any biodegradable implant material that is suitable for the manufacture of implants, in particular stent. Biodegradable materials for stent include (but are not limited to) magnesium-based alloys and zinc-based alloys.

Embodiment 2

In an alternative embodiment 2 of the present invention, the quantity of the repeat units 1 in each of the circumferential support structures 3 is between 4 and 8; the connectors 2 are spiral distribution in the longitudinal direction; the quantity of the connectors 2 between the two circumferential support structures 3 to be connected is between 2 and 4. Other composition and connection are same as the embodiment 1. By the means of increasing or decreasing the quantity of repeat units, the out diameter of stent can be resized in a large scale.

Embodiment 3

In an alternative embodiment 3 of the present invention, the height of the bump elements 11 is between 0.01 mm and 0.06 mm; the major axis of the arched elements 12 is between 0.15 mm and 0.35 mm, the minor axis of the arched elements 12 is between 0.10 mm and 0.30 mm, the width of the strut is between 0.10 mm and 0.20 mm. Other composition and connection are same as the embodiment 1.

Embodiment 4

In an alternative embodiment 4 of the present invention, the out diameter of the stent is between 1 mm and 5 mm, the thickness in the radial direction is between 0.1 mm and 0.2 mm, and the length in the longitudinal direction is between 50 mm and 100 mm. Other composition and connection are same as the embodiment 1.

Embodiment 5

In an alternative embodiment 5 of the present invention, as a result of introduction of the kink elements 14, the arched elements 12 could modified to larger radius and take more space during crimped status. Therefore, a homogeneous distribution of stress and plastic deformation in the arched elements of the stent are accomplished. The maximus principal stress and maximus residual stress reduced 5.2% and 7.6% separately, because of the benefit of the kink elements and un-uniform radius arched elements.

What is claimed is:
1. A biodegradable metallic vascular stent, comprising a base body which is tubular with a lumen along a longitudinal axis, wherein the base body has a plurality of circumferential support structures which are successively positioned along the longitudinal axis and are each composed of a sequence of repeat units, and each of the circumferential support structures connects to two or more connectors, wherein two adjacent circumferential support structures are joined together by at least one of the connectors, and each of the connectors is attached to one of arched elements of the two adjacent circumferential support structures to be connected;
wherein for the base body, an outer diameter is between 1 mm and 5 mm, a thickness in a radial direction is between 0.1 mm and 0.3 mm, a length in a longitudinal direction is between 10 mm and 100 mm; wherein for the circumferential support structures, a width of the arched elements is between 0.1 mm and 0.3 mm, a width of diagonal elements is between 0.06 mm and 0.25 mm; wherein for the connectors, a radius of a middle line of curved elements is between 0.10 mm and 0.30 mm.
2. The biodegradable metallic vascular stent as defined by claim 1, wherein the biodegradable metallic vascular stent is applicable to treatment of a peripheral vascular disease and a coronary artery disease.

* * * * *